United States Patent
Chung et al.

(10) Patent No.: US 9,517,115 B2
(45) Date of Patent: Dec. 13, 2016

(54) AMPOULE FOR STORING IMPLANT CAPABLE OF MAINTAINING HUMIDITY

(75) Inventors: Yong Il Chung, Busan (KR); Ju Dong Song, Busan (KR); Eun Jung Kang, Busan (KR); Da Mi Choi, Busan (KR); Tae Gwan Eom, Busan (KR); Kyoo Ok Choi, Seoul (KR); Su Kyoung Kim, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 110 days.

(21) Appl. No.: 14/236,652

(22) PCT Filed: Feb. 10, 2012

(86) PCT No.: PCT/KR2012/001015
§ 371 (c)(1),
(2), (4) Date: Feb. 3, 2014

(87) PCT Pub. No.: WO2013/035947
PCT Pub. Date: Mar. 14, 2013

(65) Prior Publication Data
US 2014/0166509 A1    Jun. 19, 2014

(30) Foreign Application Priority Data
Sep. 9, 2011    (KR) .................... 10-2011-0092117

(51) Int. Cl.
*A61B 19/02* (2006.01)
*A61C 8/00* (2006.01)

(52) U.S. Cl.
CPC ........... *A61C 8/0087* (2013.01); *A61C 8/0013* (2013.01)

(58) Field of Classification Search
USPC ....................................................... 206/63.5
See application file for complete search history.

(56) References Cited

U.S. PATENT DOCUMENTS 1,987,373 A * 1/1935 Shapiro .................. A24F 25/02
                                                      220/506
2,074,122 A * 3/1937 Harris .................... A24F 25/02
                                                        312/31
(Continued)

FOREIGN PATENT DOCUMENTS

EP    1523955 A1    4/2005
FR    2746629 A1    10/1997
(Continued)

OTHER PUBLICATIONS

International Search Report for International Application No. PCT/KR2012/001015.
(Continued)

*Primary Examiner* — Jacob K Ackun
(74) *Attorney, Agent, or Firm* — LRK Patent Law Firm (57) ABSTRACT

An ampoule for storing an implant capable of maintaining humidity includes: a container capable of airtight sealing at least momentarily or temporarily; a partition member which divides an accommodation space inside the container into two spaces, first and second spaces, and allows vaporized water molecules to be transported between the divided spaces; and a water molecule supply source which is accommodated in the first space of the two spaces divided by the partition member and supplies the vaporized water molecules. Therefore, the invention enables the construction of an environment which allows the hydrophilicity of the implant to be maintained for a long time, wherein the hydrophilicity is imparted to and protected from the surface of the implant or a coating layer formed on the surface of the implant.

12 Claims, 4 Drawing Sheets

(56) References Cited

U.S. PATENT DOCUMENTS

| | | | | |
|---|---|---|---|---|
| 4,366,901 | A | * | 1/1983 | Short .................... A61J 1/2096 206/210 |
| 4,969,906 | A | | 11/1990 | Kronman |
| 5,135,715 | A | * | 8/1992 | Andersen .................. A61L 2/26 239/56 |
| 5,960,956 | A | | 10/1999 | Langanki et al. |
| 6,261,097 | B1 | | 7/2001 | Schmutz et al. |
| 7,198,150 | B1 | * | 4/2007 | Blaschke ............... A61F 2/0095 206/221 |
| 2007/0084735 | A1 | * | 4/2007 | Lancesseur .......... B65D 43/164 206/204 |
| 2007/0193905 | A1 | * | 8/2007 | Jemelin .............. A61B 19/0262 206/438 |
| 2009/0018633 | A1 | * | 1/2009 | Lindquist .............. A61F 2/0095 623/1.11 |
| 2010/0179665 | A1 | * | 7/2010 | Schlottig ............... A61C 8/0087 623/23.53 |
| 2010/0243485 | A1 | | 9/2010 | Sato et al. |
| 2011/0136078 | A1 | * | 6/2011 | Ishiwata .............. A61C 8/0012 433/173 |
| 2012/0031779 | A1 | * | 2/2012 | Egued .................... A24F 25/02 206/204 |

FOREIGN PATENT DOCUMENTS

| | | |
|---|---|---|
| JP | 2000-512194 A | 9/2000 |
| JP | 2000-512195 A | 9/2000 |
| KR | 10-2011-0024641 A | 3/2011 |

OTHER PUBLICATIONS

Japanese Patent Office Action for Japanese Patent Application No. 2014-523830 which corresponds to the above-identified U.S. application.

European Search Report for European Patent Application No. 12829679 which corresponds to the above-identified U.S. application.

SIPO Office Action for Chinese Patent Application No. 201280038250.3 which corresponds to the above-identified U.S. application.

* cited by examiner

AMPOULE FOR STORING IMPLANT CAPABLE OF MAINTAINING HUMIDITY

TECHNICAL FIELD

The present invention relates to an ampoule for storing an implant capable of maintaining humidity, which can create environment capable of preserving hydrophilic property of an implant provided or protected by a coating layer formed on the surface of the implant.

BACKGROUND ART

In general, a dental implant (hereinafter, briefly called 'implant') must functionally execute role for the actual tooth because the implant is an artificial tooth permanently substituting a missing tooth. Moreover, the implant must be manufactured to be used for a long time by properly dispersing load applied to the teeth during mastication, and must be manufactured as accurate as it is little different in form and color from the actual tooth in an aspect of beauty.

The implant is transplanted and fixed into the tissue inside the oral cavity, namely, the alveolar bone, and as time goes by after transplantation into the tissue, the implant is corroded by tissue fluid or body fluid in the body or by elution of metal ions of the metal implant due to contact and friction with the tissue. Moreover, the metal ions eluted from the metal implant damage macrophages in the body or invade the cells in the body so as to cause generation of inflammatory cells or giant cells, and hence, the implant must have excellent biocompatibility.

In an aspect of materials for such an implant, there have been various attempts to use metals and alloys, but titanium metal or titanium alloys which have high bioaffinity, mechanical intensity and bio-inactivity in respect of the tissues of the human body have been mainly used.

In the meantime, for a stable osseointegration of the implant inside the body, a method of widening the surface area getting in contact with the tissue by increasing surface roughness of the implant has been used. The SA (Sandblasting with large grit and Acid treatment) method which is a representative method for increasing the surface area of the implant blasts $Al_2O_3$ particles onto the surface of the implant in order to generate craters and micro-pits, and then, treats strong acid ($H_2SO_4$/HCl), and hence, as a result, has an effect to increase the surface area by more than 40 percent in comparison with the conventional RBM (Resorbable Blasting Media) method. Therefore, the implant produced by the SA method after blasting of the particles can reduce the average curing period by six weeks to eight weeks from twelve weeks.

However, the surface of hydrophilic titanium surface-treated by the SA method has a demerit in that it is rapidly hydrophobized by irreciprocal absorption of carbon pollution sources in the air.

Because the hydrophobized surface hinders an inflow of bone cells to the surface of the implant so as to reduce a contact ratio between the bone and the implant from the beginning of the implant procedure, it may be a potential cause of failure of the implant procedure.

Therefore, countermeasures for maintaining the hydrophilic property by preventing hydrophobization of the surface of the titanium implant manufactured by the SA method in the air have been prepared. A representative countermeasure of the countermeasures is to cut off contact with the air by putting and packing the titanium implant into a container filled with water or inert gas so as to cut off contact with the air.

The above packing method is very effective in an aspect of maintaining hydrophilic property of the surface of the titanium implant, but there is a restriction in use front the standpoint of the recent development direction of implants. That is, the recent development point of implants is to reduce the period of the implant procedure by coating the surface of the implant with chemical material, peptide or protein which can promote osseointegration. However, there is no verification on what happens when the implant which is coated with such a material is covered with water, and if it has a bad influence on the implant, it is necessary to look for another packing media which can solve the above-mentioned problem.

Therefore, with a new concept different from the packing method for creating the conventional inert environment, a development of a new implant packing which can prevent hydrophobization of the surface of the implant and maintain the hydrophilic property of the surface is needed.

DISCLOSURE

Technical Problem

Accordingly, the present invention has been made in an effort to solve the above-mentioned problems occurring in the prior arts, and it is an object of the present invention to provide an ampoule for storing an implant capable of maintaining humidity, which can create environment capable of preserving hydrophilic property of an implant provided or protected by a coating layer formed on the surface of the implant.

Technical Solution

To achieve the above objects, the present invention provides an ampoule for storing an implant capable of maintaining humidity including: a container capable of sealing with airtightness at least momentarily or temporarily; and a partition member dividing an accommodation space inside the container into two spaces, first and second spaces, and allowing vaporized water molecules to move between the divided spaces, wherein a water molecule supply source which is accommodated in the first space of the two spaces for supplying the vaporized water molecules, and an implant is held in the second space.

Here, the partition member includes a vent hole which forms a flow channel of the vaporized water molecules.

Moreover, the partition member includes a separation membrane which allows a movement of the vaporized water molecules between the partitioned spaces.

Furthermore, at least one portion of the implant is protrudingly inserted and fixed into the second space.

In the meantime, a hydrophilic coating layer is formed on at least one portion of the surface of the implant.

The hydrophilic coating layer may be made of a material containing sugar alcohol, and the sugar alcohol is at least one selected from a group consisting of glycerol, solbitol, xylitol, mannitol, maltitol, and lactitol.

Additionally, the hydrophilic coating layer may be a film containing one or more buffering material selected from a group consisting of ACES, BES, CHES, HEPES, MOPS, PIPES and TES which are organic amphoteric ion buffering materials having a sulfonic acid group.

In addition, the hydrophilic coating layer may be a film containing one or more phosphate-based inorganic salt selected from monosodium phosphate, disodium phosphate, trisodium phosphate, calcium phosphate, and a group containing the above-mentioned materials.

Moreover, the hydrophilic coating layer may be a film formed of glycerol phosphate or glycerol phosphate-based organic salt.

Meanwhile, the separation membrane is made of a porous material.

Here, the porous material contains at least one selected from a group consisting of PVDF (Polyvinylidene fluoride), PES (Polyether sulfone), MCE (Mixed cellulose esters), cellulose acetate, nitrocellulose, polycarbonate, PTFE (Polytetrafluoro-ethylene), PP (Polypropylene), PVC (Polyvinyl chloride), nylon, and glass and quartz fiber.

Furthermore, the water molecule supply source contains moisture by adding water to at least one material selected from a group consisting of polyacrylic acid, polyvinyl alcohol, polyethylene glycol, carboxylmethylene cellulose or hyaluronic acid.

In an aspect of the present invention, the container includes an openable lid and a main body airtightly joined with the lid, and the first space is formed in the lid and the second space is formed in the main body.

Additionally, the partition member is arranged crossing between the lid and the main body, and is a separation membrane which allows a movement of the vaporized water molecules between the partitioned spaces. Alternatively, the partition member is formed integrally with the lid, and the lid comprises a vent hole forming a flow channel of the vaporized water molecules by communicating the first space and the second space with each other.

Moreover, the main body includes an inner case and an outer case each of which is concentrically arranged relative to the lid and airtightly joined to the lid 110, and the inner case surrounded by the outer case forms the second space.

Furthermore, the inner case has a cut surface formed in at least one portion thereof such that the inner case and the outer case form the second space together.

Here, the cut surface has a hole formed in one portion thereof to which the implant held in the second space is fixed.

Additionally, the inner case or the outer case is airtightly joined with the lid by screw-coupling or protrusion-slot connection.

Advantageous Effects

The ampoule for storing an implant capable of maintaining humidity according to the exemplary embodiment of the present invention can maintain humidity of the two spaces in a dynamic equilibrium state because the vaporized water molecules supplied from the water molecule supply source freely move between the first and second spaces, and thus, can create environment capable of preserving hydrophilic property of the implant, which is provided or protected by a coating layer formed on the surface of the implant, for a long time.

MODE FOR INVENTION

Hereinafter, reference will be now made in detail to an ampoule 10 for storing an implant capable of maintaining humidity according to a preferred embodiment of the present invention with reference to the attached drawings.

In the present invention, description of the same configuration and action as the prior arts will be omitted.

In the description of the present invention, when it is judged that detailed descriptions of known functions or structures related with the present invention may make the essential points vague, the detailed descriptions of the known functions or structures will be omitted.

In addition, in the drawings, it will be understood that thickness of lines or sizes of components illustrated in the drawings may be exaggerated for clarity and convenience in explanation. Additionally, the terms indicating relative positions, such as 'front and rear', 'up and down and left and right', and 'inside and outside', are based on the directions illustrated in the drawings.

Figure 1:
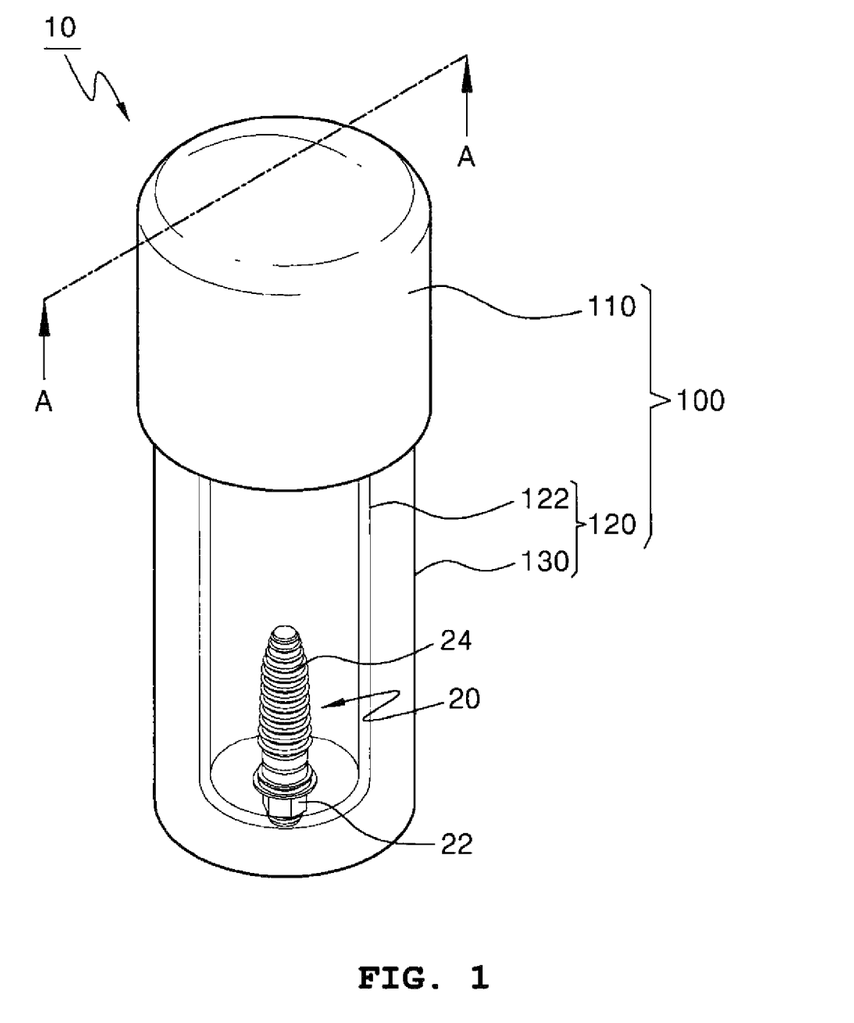
FIG. 1 is a perspective view showing an outward appearance of an ampoule for storing an implant capable of maintaining humidity according to a preferred embodiment of the present invention.
Figure 2:
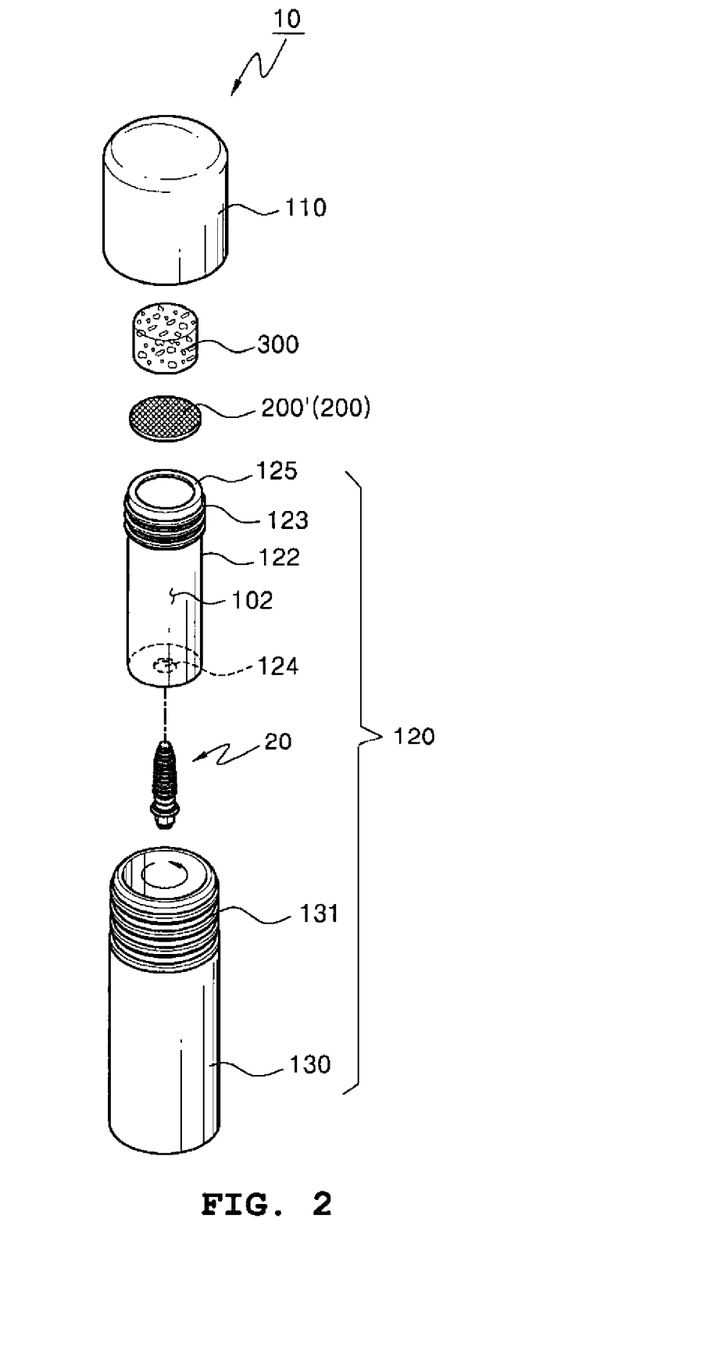
FIG. 2 is an exploded perspective view of the ampoule capable of maintaining humidity of FIG. 1.
Figure 3:
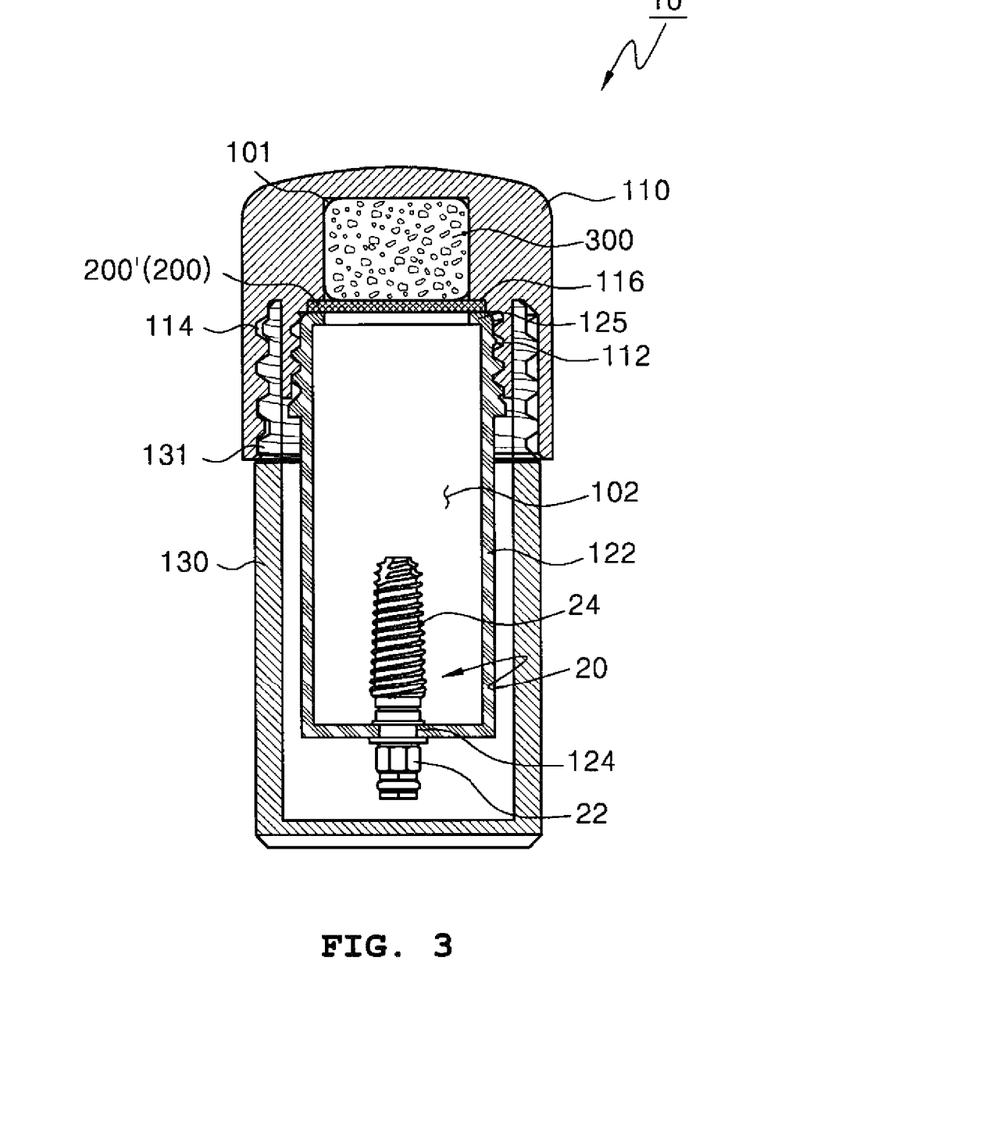
FIG. 3 is a sectional view taken along the line of A-A of FIG. 1.

The ampoule 10 for storing the implant capable of maintaining humidity according to the preferred embodiment of the present invention illustrated in FIGS. 1 to 3 is a container 100 which is capable of sealing with airtightness at least momentarily or temporarily. A space inside the container 100 is divided into two spaces by a separation membrane 200' which is a partition member 200. Here, the expression, "to be capable of sealing with airtightness at least momentarily or temporarily' means that the airtight sealing of the container 100 is possible not only once but also repeatedly.

The partition member 200 is a member which divides the inside space of the container 100 into two spaces, namely, a first space 101 and a second space 102, and allows a free movement of vaporized water molecules. As the partition member 200, a separation membrane 200' made of a porous material may be selected. The porous material for the separation membrane 200 may be at least one selected from a group consisting of PVDF (Polyvinylidene fluoride), PES (Polyether sulfone), MCE (Mixed cellulose esters), cellulose acetate, nitrocellulose, polycarbonate, PTFE (Polytetrafluoro-ethylene), PP (Polypropylene), PVC (Polyvinyl chloride), nylon, and glass and quartz fiber.

As described above, the partition member 200 is divided into the two spaces, namely, the first space 101 and the second space 102. A water molecule supply source 300 is accommodated in the first space 101. The water molecule supply source 300 is to supply vaporized water molecules inside the limited space of the container 100, and the vaporized water molecules can freely pass between the first and second spaces 101 and 102 through the separation membrane 200' of the partition member 200, and hence, humidity inside the first and second spaces 101 and 102 can be kept in a dynamic equilibrium state. That is, even though the water molecule supply source 300 is accommodated in the first space 101 in a state where it is isolated by the partition member 200, humidity of the second space 102 is also dynamically controlled by the water molecule supply source 300, and the water supply source 300 reversibly discharges or absorbs water molecules.

It is preferable that a material capable of containing a sufficient quantity of moisture be selected as the water molecule supply source 300, and for instance, the water molecule supply source 300 may contain moisture by adding water to at least one material selected from a group consisting of polyacrylic acid, polyvinyl alcohol, polyethylene glycol, carboxylmethylene cellulose or hyaluronic acid.

In the meantime, an implant 20 is held in the second space 102. Here, at least one portion of the surface of the implant 20, preferably, the surface of a fixture 24 of the implant 20 which is implanted into the alveolar bone of a human body and gets in contact with the tissue has a hydrophilic coating layer.

If a roughness of a microunit is formed on the surface of the implant, the surface area is increased so as to enhance osseointegration of the implant, but pollution due to sources of pollution in the air is also increased in proportion to the increased surface area during the storage of the implant till the dental procedure. For instance, carbon pollution sources, such as carbon dioxide and organic carbon, existing in the air are irreversibly absorbed to the surface of the implant so as to hydrophobize the surface of the implant. When the implant is transplanted into the body in the hydrophobized state, biocompatibility is reduced, for instance, various kinds of protein existing in the blood are not attached to the surface of the implant, and hence, it may cause a problem in osseointegration and an inflammatory response by the pollution sources. Therefore, in order to prevent the hydrophobization due to absorption of the pollution sources onto the surface of the implant 20, hydrophilic coating layers of various kinds may be formed.

The hydrophilic coating layer can keep the hydrophilic property of the surface of the implant 20 for a period of time, but may be destroyed in a long-term dried environment. Therefore, it is preferable to keep environment around the implant 20 in a properly wet condition, but if the implant 20 is kept in an excessively wet condition for a long time, it may cause an alteration of the coating layer or may have a bad influence on uncoated portions of the implant 20.

In consideration of such various requirements, the inside space of the container 100 is divided into the first and second spaces 101 and 102 by the partition member 200, and the water molecule supply source 300 is put in the first space 101 and the implant 20 having the hydrophilic coating layer is held in the second space 102. As described above, because the vaporized water molecules can freely pass between the first and second spaces 101 and 102 through the partition member 200, humidity in the two spaces can keep the dynamic equilibrium state, and so with the case that the implant 20 is held in the second space 102.

In other words, when the hydrophilic coating layer of the implant 20 accommodated in the second space 102 absorbs surrounding moisture (vaporized water molecules) in a dried condition, humidity of the second space 102 becomes low, and hence, in order to keep the equilibrium state with the first space 101, water molecules are supplied from the water molecule supply source 300, and in the opposite case, the water molecule supply source 300 absorbs water molecules, and hence, humidity of the first and second spaces 101 and 102 keeps the dynamic equilibrium state.

In an aspect of the present invention, the hydrophilic coating layer formed on the surface of the implant 20 may be a film for keeping the wet condition or the dried condition at room temperature. Particularly, the hydrophilic coating layer which is a moisturizing film for keeping the wet condition at room temperature can prevent hydrophobization of the implant 20 for a long time in a moisturized condition, it may be evaluated that the hydrophilic coating layer is very suitable for the present invention.

Such a hydrophilic coating layer may be formed by being coated with a solution containing sugar alcohol or being soaked in the solution containing sugar alcohol, and the sugar alcohol forming the hydrophilic coating layer may be one selected from a group consisting of glycerol, solbitol, xylitol, mannitol, maltitol, and lactitol.

As the material for forming the hydrophilic coating layer, at least one buffering material selected from a group consisting of ACES, BES, CHES, HEPES, MOPS, PIPES and TES which are organic amphoteric ion buffering materials having a sulfonic acid group.

Moreover, the hydrophilic coating layer may be formed with a film containing at least one phosphate-based inorganic salt selected from monosodium phosphate, disodium phosphate, trisodium phosphate, calcium phosphate, and a group containing one of the above-mentioned materials or a film formed of glycerol phosphate or glycerol phosphate-based organic salt.

The above-mentioned materials can prevent hydrophobization of the surface of the implant 20 and absorb moisture, and hence, can effectively accept water molecules supplied from the water molecule supply source 300.

Meanwhile, as shown in FIGS. 2 and 3, the container 100 in which the implant 20 is accommodated includes an operable lid 110 and a main body 120 airtightly covered with the lid 110. The first space 101 in which the water molecule supply source 300 is accommodated is formed in the lid 110, and the second space 102 in which the implant 20 is held is formed in the main body 120. In this instance, the separation membrane 200' which is the partition member 200 is arranged crossing a joining surface between the lid 110 and the main body 120.

Furthermore, it is also possible to arrange the first space 101 in the upper part (lid) of the container 100 and the second space 102 in the lower part (main body) of the container 100. In the case that the container 100 is small, the implant 20 which is relatively heavier is held at the lower part of the container 100 so as to easily keep the balance of the container 100 by lowering the center of the entire gravity.

Moreover, in the preferred embodiment of the present invention, the container 100 may have a double structure including an inner case 122 and an outer case 130 surrounding the inner case 122, each of which is concentrically arranged relative to the lid 110 and airtightly joined to the lid 110. In this instance, the inner case 122 surrounded by the outer case 130 forms the second space 102 in which the implant 20 is accommodated, and the separation membrane 200' is arranged crossing the joining surface between the lid 110 and the inner case 122.

The separation membrane 200' is fixed when the separation membrane 200' is seated on a stepped jaw 116 formed on the lid 110 and the upper face of the inner case 122 presses the separation membrane 200'. A bent portion 125 is formed on the upper face of the inner case 122 so as to widen a contact area with the separation membrane 200', such that the separation membrane 200' can keep airtightness stably without any damage. The main body 120 of the double structure can effectively enhance airtightness of the container 100 and securely protect the implant 20 from an external shock.

Additionally, the main body 120 may include an inner case 122 and an outer case 130 which are made of a transparent material, such that a user can check the condition of the hydrophilic coating layer with naked eyes.

Particularly, the implant 20 passes through a joining hole 124 formed in the bottom face of the inner case 122 and a portion of the implant 20 is protrudingly inserted and fixed into the second space 102, and more preferably, a portion, for instance, the fixture part, of the implant 20 having the hydrophilic coating layer may be protrudingly inserted and fixed into the second space 102. Such a structure has a merit in that it can prevent that the container 100 is reversed by shaking of the implant 20 because the implant 20 is fixedly held in the inner case 122 and has a more important merit in that water molecules supplied by the water molecule supply source 300 to the hydrophilic coating layer can be more concentrated on the fixture 24 because only a portion, for instance, the fixture 24 illustrated in FIG. 3, of the implant having the hydrophilic coating layer is accommodated in the second space 102.

In the meantime, in order to detachably assemble the lid 110 with the main body 120 of the container 100, a first male screw portion 123 formed on the upper portion of the inner case 122 and a second male screw portion 131 formed on the upper portion of the outer case 130 may be respectively screw-coupled to a first female screw portion 112 and a second female screw portion 114 concentrically formed on the lid 110. Through the above structure, in response to the diameters of the inner case 122 and the outer case 130, the first female screw portion 112 is smaller in diameter than the second female screw portion 114.

Figure 4:
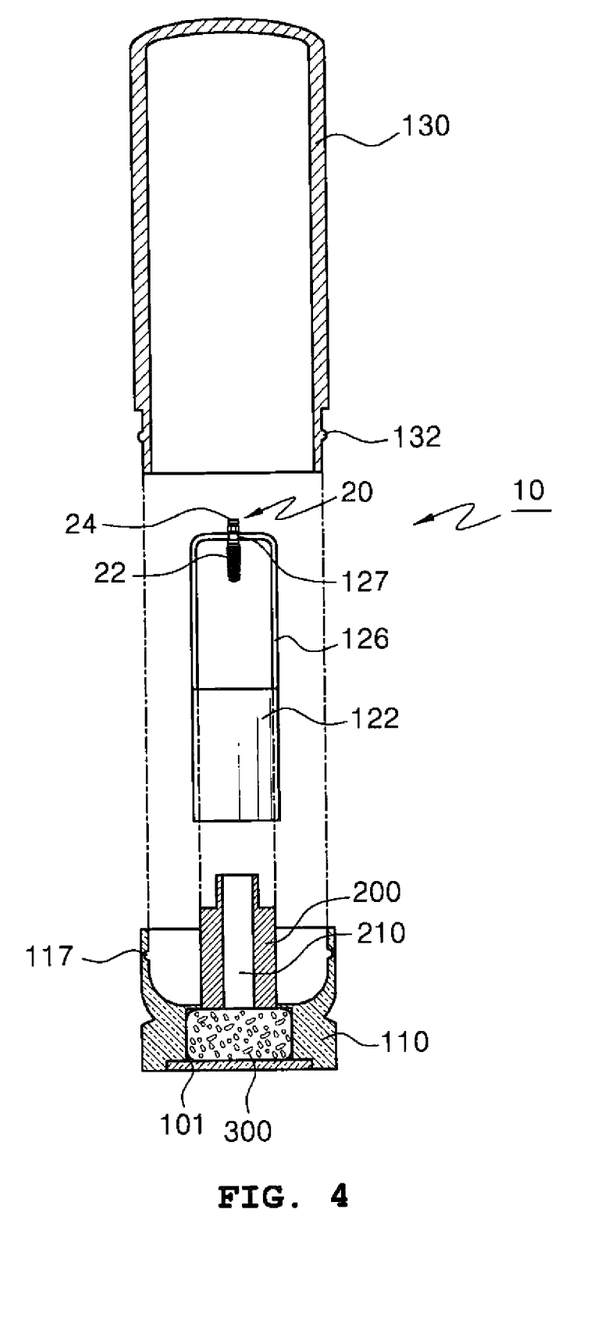
FIG. 4 is a view showing a structure of an ampoule for storing an implant capable of maintaining humidity according to another preferred embodiment of the present invention.

In the meantime, FIG. 4 illustrates an ampoule 10 for storing an implant capable of maintaining humidity according to another preferred embodiment of the present invention. Focused on parts different from those of the first preferred embodiment described referring to FIGS. 1 to 3, this embodiment referring to FIG. 4 will be described and repeated parts will be omitted.

The biggest difference of this embodiment from the first preferred embodiment is that the ampoule does not have the partition member 200 formed integrally with the lid 110 but has a vent hole 210 which communicates the first space 101 and the second space 102 with each other, such that a flow channel of the water molecules vaporized in the water molecule supply source 300 is formed. That is, in this embodiment referring to FIG. 4, instead of the separation membrane 200', the vent hole 210 is disposed in order to freely move the vaporized water molecules between the first space 101 formed in the lid 110 and the second space 102 formed in the inner case 122.

In this embodiment, there is another difference in that the inner case 122 has a cut surface 126 formed on at least one portion of the inner case 122 so as to form the second space 102 between the inner case 122 and the outer case 130 and a hole 127 formed at one portion of the cut surface 126 such that the implant 20 can be inserted and fixed into the hole 127. Because the hole 127 is formed in the cut surface 126, the second space 102 is a little expanded by the cut surface 126 but it provides convenience in use because the user can easily insert and remove the implant 20.

Moreover, the inner case 122 and the outer case 130 can be fixed to the lid 110 not by screw-coupling (112-123 and 114-131) but by protrusion-slot (132-117) connection. In FIG. 4, the outer case 130 has a protrusion 132 formed on the outer circumferential surface of the front end and the lid 110 has a slot 117 formed in the inner circumferential surface thereof in correspondence with the protrusion 132. Of course, for airtight combination between the lid 110 and the inner and outer cases 122 and 130, a close contact between contact surfaces is important, but as shown in FIG. 4, the airtight joining and sealing can be achieved just by a close contact between the lid 110 and the inner case 122. Here, FIG. 4 illustrates an example that the inner circumferential surface of the inner case 122 is closely joined to the outer surface of the partition member 200 formed integrally with the lid 110.

Besides, FIG. 4 illustrates an example that the lid 110 is arranged at the lower part of the container 100 and an exposed lower surface of the lid 110 is flat. In this embodiment, the ampoule has a merit in that the user can easily observe the implant 20 located at the upper part when a plurality of the ampoules 10 capable of maintaining humidity are packed with one box.

As described above, while the present invention has been particularly shown and described with reference to the example embodiments thereof, it will be understood by those of ordinary skill in the art that the above exemplary embodiments of the present invention are all exemplified and various changes, modifications and equivalents may be made therein without changing the essential characteristics and scope of the present invention.

The invention claimed is:

1. An ampoule for storing an implant and maintaining humidity, comprising:
   an implant;
   a container sealing with airtightness at least momentarily or temporarily and comprising an openable lid and a main body, which are airtightly joined to each other;
   a partition member dividing a room inside the container into first and second spaces and allowing vaporized water molecules to move between the first and second spaces; and
   a water molecule supply source supplying the vaporized water molecules,
   wherein the main body comprises an inner case and an outer case, each of which is concentrically arranged relative to the lid and airtightly joined to the lid, the inner case being surrounded by the outer case and forming the second space,
   wherein the partition member is disposed crossing between the lid and the main body so that the lid and the main body are separated from each other,
   wherein the water molecule supply source is disposed in the first space, and said implant is disposed in the second space,
   wherein at least a portion of said implant is protrudingly inserted and fixed into the second space,
   wherein a hydrophilic coating layer is formed on at least a portion of a surface of said implant, and
   wherein the first space is formed in the lid, and the second space is formed in the main body.

2. The ampoule according to claim 1, wherein the partition member comprises a separation membrane which allows movement of the vaporized water molecules between the first and second spaces.

3. The ampoule, according to claim 1, wherein the hydrophilic coating layer is made of a material containing sugar alcohol.

4. The ampoule according to claim 3, wherein the sugar alcohol is at least one selected from a group consisting of glycerol, solbitol, xylitol, mannitol, maltitol, and lactitol.

5. The ampoule according to claim 1, wherein the hydrophilic coating layer is a film containing one or more buffering material selected from a group consisting of ACES, BES, CHES, HEPES, MOPS, PIPES and TES which are organic amphoteric ion buffering materials having a sulfonic acid group.

6. The ampoule according to claim 1, wherein the hydrophilic coating layer is a film containing one or more phosphate-based inorganic salt selected from monosodium phosphate, disodium phosphate, trisodium phosphate, calcium phosphate, and a group containing the above-mentioned materials.

7. The ampoule according to claim 1, wherein the hydrophilic coating layer is a film formed of glycerol phosphate or glycerol phosphate-based organic salt.

8. The ampoule according to claim 2, wherein the separation membrane is made of a porous material.

9. The ampoule according to claim 8, wherein the porous material contains at least one selected from a group consisting of PVDF (Polyvinylidene fluoride), PES (Polyether sulfone), MCE (Mixed cellulose esters), cellulose acetate, nitrocellulose, polycarbonate, PTFE (Polytetrafluoro-ethylene), PP (Polypropylene), PVC (Polyvinyl chloride), nylon, and glass and quartz fiber.

10. The ampoule according to claim 1, wherein the water molecule supply source contains moisture by adding water to at least one material selected from a group consisting of polyacrylic acid, polyvinyl alcohol, polyethylene glycol, carboxylmethylene cellulose or hyaluronic acid.

11. The ampoule according to claim 1, wherein the partition member is a separation membrane which allows movement of the vaporized water molecules between the first and second spaces.

12. The ampoule according to claim 1, wherein the inner case or the outer case is airtightly joined to the lid by screw-coupling or protrusion-slot connection.

* * * * *